(12) United States Patent
Higuchi et al.

(10) Patent No.: US 7,070,583 B1
(45) Date of Patent: Jul. 4, 2006

(54) MEDICAL BEVEL NEEDLE

(75) Inventors: Akio Higuchi, Tokyo (JP); Hayato Hyugaji, Tokyo (JP)

(73) Assignee: Dr. Japan Co., Ltd., Tokyo (JP)

( * ) Notice: Subject to any disclaimer, the term of this patent is extended or adjusted under 35 U.S.C. 154(b) by 599 days.

(21) Appl. No.: 10/311,970

(22) PCT Filed: Jul. 3, 2000

(86) PCT No.: PCT/JP00/04394

§ 371 (c)(1),
(2), (4) Date: Dec. 23, 2002

(87) PCT Pub. No.: WO02/02161

PCT Pub. Date: Jan. 10, 2002

(51) Int. Cl.
*A61M 5/32* (2006.01)

(52) U.S. Cl. .................. 604/274; 604/164.06; 604/272
(58) Field of Classification Search ............... 604/19, 604/20, 21, 22, 27, 48, 93.01, 57, 164.01, 604/164.06, 264, 272, 274
See application file for complete search history.

(56) References Cited

U.S. PATENT DOCUMENTS

| | | | | |
|---|---|---|---|---|
| 3,308,822 A | * | 3/1967 | De Luca | 604/274 |
| 4,490,139 A | * | 12/1984 | Huizenga et al. | 604/57 |
| 5,575,780 A | | 11/1996 | Saito | |
| 5,752,942 A | | 5/1998 | Doyle et al. | |
| 5,820,609 A | * | 10/1998 | Saito | 604/272 |
| 5,968,022 A | * | 10/1999 | Saito | 604/272 |
| 6,009,933 A | * | 1/2000 | Doyle et al. | 163/5 |
| 6,517,523 B1 | * | 2/2003 | Kaneko et al. | 604/272 |

FOREIGN PATENT DOCUMENTS

| | | |
|---|---|---|
| JP | 38-5396 B1 | 5/1963 |
| JP | 54-168092 U | 11/1979 |

* cited by examiner

*Primary Examiner*—Brian L. Casler
*Assistant Examiner*—Jennifer Maynard
(74) *Attorney, Agent, or Firm*—Birch, Stewart, Kolasch & Birch, LLP

(57) ABSTRACT

A medical bevel needle (1) having an open bevel end surface 3 is provided, wherein cutting edges (9) that linearly extend from the front end of the front-end portion (2) on the right and left sides diagonally rearwardly are formed either by right and left front ground faces (5) crossing the open bevel end surface (3) or by right and left front ground faces (5) crossing the external circumferential surface (4) of the bevel needle (1), and the maximum lateral width between the cutting edges is limited by right and left rear ground surfaces (6). When the needle axis is held horizontal with the open bevel end surface (3) facing upward, the right and left front ground surfaces (5) cross each other at the front end of the front-end portion (2), and extend diagonally rearwardly and symmetrically with respect to a vertical plane containing the needle axis, where the right and left rear ground surfaces (6), respectively succeed the right and left front ground surfaces (5) at a longitudinal position where the lateral width between the right and left front ground surfaces (5) reaches a specified length, e.g., a length equal to the radius of the bevel needle, and extend diagonally rearwardly and symmetrically with respect to the vertical plane at an angle smaller than the angle of the right and left front ground surfaces (5) with respect to the vertical plane. The right and left rear ground surfaces (6) respectively have a tilt angle of 5π/12 to π/2 radians (75 to 90 degrees) with respect to the horizontal plane.

7 Claims, 5 Drawing Sheets

MEDICAL BEVEL NEEDLE

This application is the national phase under 35 U.S.C. §371 of PCT International Application No. PCT/JP00/04394 which has an International filing date of Jul. 3, 2000, which designated the United States of America.

TECHNICAL FIELD

The present invention relates to a medical bevel needle having cutting edges formed on the front-end portion of an open bevel end surface thereof. This bevel needle is used when medicinal injections or blood-drawings are conducted for medical treatment or inspection.

BACKGROUND TECHNOLOGY

A conventional bevel needle used for medicinal injections or blood-drawings has cutting edges in the front-end portion of the bevel needle, where the cutting edges are of an acute pointed-arch shape with a semi-circular profile along the external circumferential surface of the bevel needle when seen from front. When the needle axis is held horizontal with the open bevel end surface facing upward, these cutting edges are formed by right and left ground surfaces that cross the external circumferential surface of the bevel needle or by right and left ground surfaces that cross the open bevel end surface of the bevel needle. The right and left ground surfaces cross each other at the front end of the bevel needle and extend diagonally rearwardly and symmetrically with respect to a vertical plane containing the needle axis. Both the right and left side ends of the cutting edges have acute apex angles.

Because of having acute cutting edges, such a conventional bevel needle enables easy puncturing but causes a semi-circular wound in bio-tissue, such as a dura mater and a blood vessel punctured. The semi-circular wound not only tends to curl up, thereby causing lengthened time for curing, but also, when a blood vessel is punctured, the semi-circular wound in the blood vessel wall would curl up causing medicinal solution injected into the blood vessel to leak into the patient's body, and, when a subarachnoid space is punctured, the semi-circular wound in the covering dura mater would curl up causing spinal fluid to leak into the patient's body, thereby inflicting a long-time pain on the patient.

The present invention is made to solve the problem described above. Thus, an object of the present invention is to provide a medical bevel needle that enables easy puncturing but does not cause a semi-circular wound in the bio-tissue punctured that tends to curl up.

DISCLOSURE OF THE INVENTION

To accomplish the object described above, means are provided, according to the present invention, such that right and left rear ground surfaces are provided on a hollow bevel needle that limit the maximum lateral width between cutting edges to a specified length, e.g., a length equal to, or less than, the radius of the bevel needle, where the cutting edges are formed by right and left front ground surfaces. The maximum lateral width between cutting edges herein means the maximum lateral width, lateral to a vertical plane containing the needle axis, between the lateral outside ends of right and left cutting edges.

When the needle axis of the hollow bevel needle is held horizontal with an open bevel end surface thereof, disposed on the front-end portion of the bevel needle, facing upward, the right and left front ground surfaces cross each other at the front end thereof, and extend diagonally rearwardly and symmetrically with respect to a vertical plane containing the needle axis. The right and left rear ground surfaces extend diagonally rearwardly and symmetrically with respect to the vertical plane at an angle smaller than the angle of the right and left front ground surfaces with respect to the vertical plane. The right and left rear ground surfaces respectively tilt at an angle of $5\pi/12$ to $\pi/2$ radians (75 to 90 degrees) with respect to the horizontal plane. The open bevel end surface crosses the vertical plane at a right angle, and tilts backward at an angle of $\pi/9$ to $\pi/4$ radians (20 to 45 degrees) with respect to the horizontal plane, thereby defining the position for medicinal injection or blood-drawing.

In cross sections crossing the needle axis at a right angle, the right and left front ground surfaces form respective triangle-like profiles protruding right-and leftwards by either crossing the external circumferential surface of the bevel needle or by crossing the open bevel end surface. Because of having an acute apex angle, these triangle-like profiles form respective acute cutting edges. The right and left rear ground surfaces succeeding the right and left front ground surfaces, form respective truncated-angled or trapezoidal profiles protruding right and leftwards by crossing the front ground surfaces and by crossing the external circumferential surface of the bevel needle and by crossing the open bevel end surface. Because of the two corner angles thereof being either obtuse or right angles, these trapezoidal profiles do not form cutting edges.

As described above, the front-end portion of the bevel needle has acute cutting edges until they come to a longitudinal position where the lateral width of the bevel needle reaches a specified length, e.g., a length equal to the radius of the bevel needle, and these acute cutting edges cause a wound by cutting bio-tissue when punctured. As seen from front, these cutting edges have the shape of a circular arc with a narrow central angle and the same radius as the radius of the bevel needle. Such a narrow central angled circular arc is close to a straight line when, for example, the central angle is as narrow as $\pi/3$ radians (60 degrees), which is the case with the lateral width of the bevel needle being the same as the radius of the bevel needle. Consequently, the wound caused in the bio-tissue when punctured by such cutting edges has the shape of a circular arc close to a straight line.

The front-end portion of the bevel needle where the lateral width thereof is equal to, or greater than, a specified length, e.g., a length equal to the radius of the bevel needle, does not form cutting edges, and is consequently not likely to cut the bio-tissue punctured Thus, a wound caused in a blood vessel or dura mater punctured by a bevel needle of the present invention, is of the shape of a narrow central angled circular arc close to a straight line, and would not curl up. Consequently, medicinal solution and spinal fluid inside the bio-tissue are not likely to leak out into the patient's body and thereby inflict pain on the patient. Therefore, a quick recovery from the wound is also enabled.

BEST EMBODIMENTS OF THE INVENTION

Figure 1:
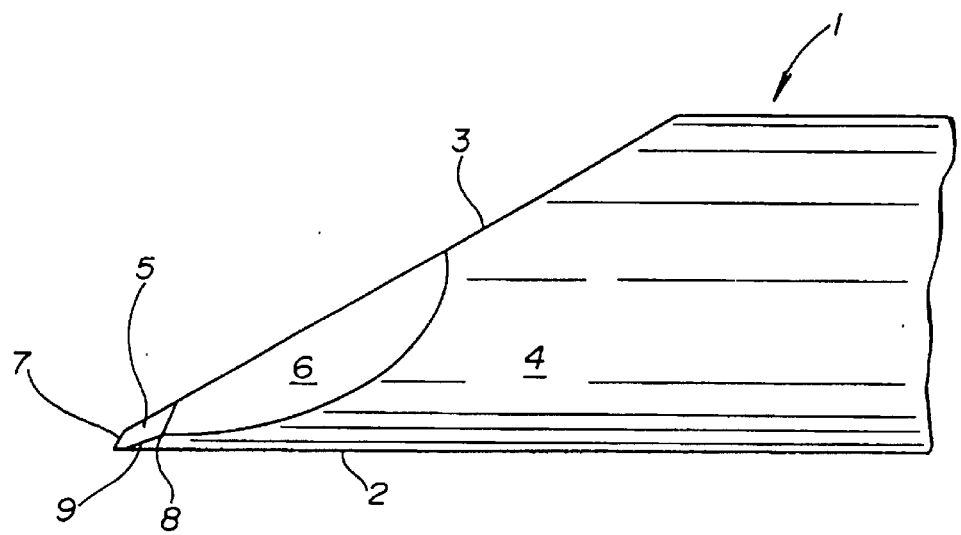
FIG. 1 is a side view of a first embodiment of a hollow bevel needle, according to the present invention.

Now, the present invention will be explained in detail, based on embodiments shown in the drawings.

A hollow bevel needle has a construction such that an open bevel end surface is disposed on the front-end portion of a hollow tube by cutting the hollow tube diagonally, where cutting edges are formed by grinding the front end of the open bevel end surface.

Figure 2:
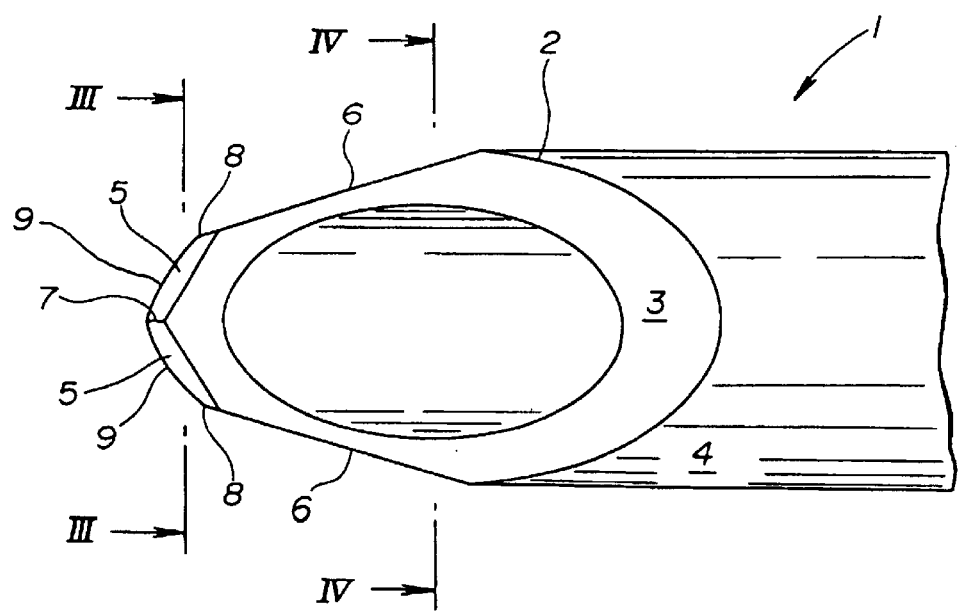
FIG. 2 is a plan view of the first embodiment.

As shown in FIGS. 1 and 2, in a hollow bevel needle 1 of a first embodiment of the present invention, when the needle axis thereof is held horizontal with an open bevel end surface 3 thereof facing upward, the external circumferential end of the open bevel end surface 3 on the front-end portion 2 forms right and left bent lines respectively positioned symmetrically with respect to a vertical plane containing the needle axis. The front-end portion 2 includes the open bevel end surface 3, the external circumferential surface 4 of the bevel needle 1, right and left front ground surfaces 5, and right and left rear ground surfaces 6. The open bevel end surface 3 crosses the vertical plane containing the needle axis at a right angle, and tilts backward at an angle of about π/6 radians (about 30 degrees) with respect to the horizontal plane. The right and left rear ground surfaces 6 cross the horizontal plane at a right angle, and tilt at an angle of about π/12 radians (about 15 degrees) with respect to the vertical plane.

The right and left front ground surfaces 5 are symmetrical with respect to the vertical plane containing the needle axis, cross each other at the front end of the front-end portion 2, and extend rearwardly, with the upper and front ends thereof tilted toward the vertical plane. The right and left front ground surfaces 5 form a backward-tilting front edge line 7, with the lower end thereof positioned forward relative to the upper end thereof, and the upper end of the front edge line 7 constitutes the front end of the open bevel end surface 3. The right and left front ground surfaces 5 also form cutting edges 9 that extend diagonally rearwardly on the right and left, by crossing the external circumferential surface 4 of the bevel needle 1.

The right and left rear ground surfaces 6 extend diagonally rearwardly and symmetrically at an angle smaller than the angle of the right and left front ground surfaces 5 with respect to the vertical plane. The right and left rear ground surfaces 6 cross the horizontal plane at a right angle. The lateral width between the right and left rear ground surfaces 6 at the front ends 8 thereof is equal to, or less than, the radius of the bevel needle. The lateral width between the right and left rear ground surfaces 6 herein means the lateral width between the lateral outside ends of the right and left rear ground surfaces 6.

Figure 3:
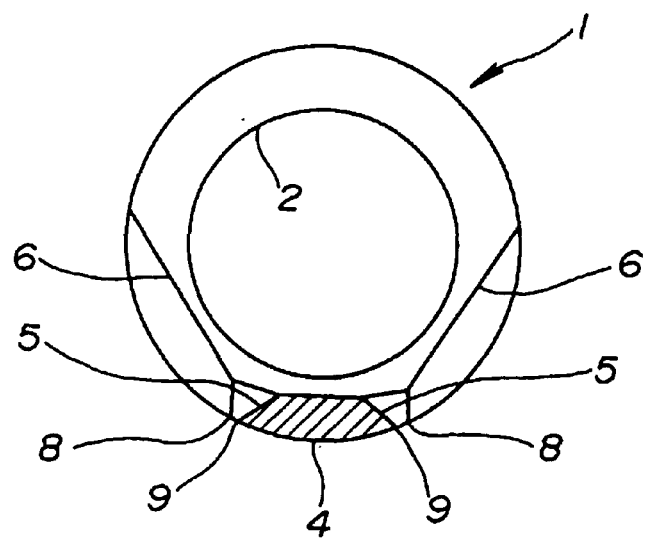
FIG. 3 is a cross-sectional view along arrow lines III—III of FIG. 2.

As shown in FIG. 3, at longitudinal positions ahead of the front end 8 of the right and left rear ground surfaces 6 of the front-end portion 2, both sides of the front-end portion 2 include the right and left front ground surfaces 5 and the external circumferential surface 4 of the bevel needle 1, where the both sides of the front end-portion 2 protrude right-and leftwards, forming respective triangle-like profiles, in cross sections crossing the needle axis at a right angle. Because of having an acute apex angle, the both sides of the front-end portion 2 at longitudinal positions ahead of the front end 8 of the right and left rear ground surfaces 6 of the front-end portion 2, form respective acute cutting edges 9.

Figure 4:
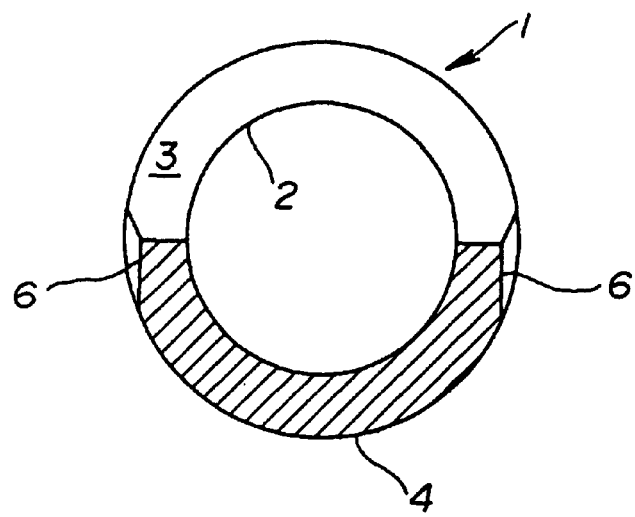
FIG. 4 is a cross-sectional view along arrow lines IV—IV of FIG. 2.

As shown in FIG. 4, however, at longitudinal positions behind the front end 8 of the right and left rear ground surfaces 6 on the front-end portion 2, both sides of the front-end portion 2 include the right and left front ground surfaces or the open bevel end surface 3, the right and left rear ground surfaces 6 and the external circumferential surface 4 of the bevel needle 1. The both sides of the front-end portion 2 protrude right-and leftwards, forming respective trapezoidal profiles, in cross sections crossing the needle axis at a right angle. Because of the two corners thereof each having a right angle in the upper corner and an obtuse angle in the lower corner thereof, these trapezoidal profiles do not form cutting edges. As a result, the maximum lateral width between the right and left cutting edges 9 is limited by the lateral width between the front ends 8 of the right and left rear ground surfaces 6. When the lateral width between the front ends 8 is set to be equal to, or smaller than, the radius of the bevel needle 1, the circular arc formed by the cutting edges 9 is of a shape close to a straight line, where the central angle of the circular arc is equal to, or smaller than, π/3 radians (60 degrees).

Figure 5:
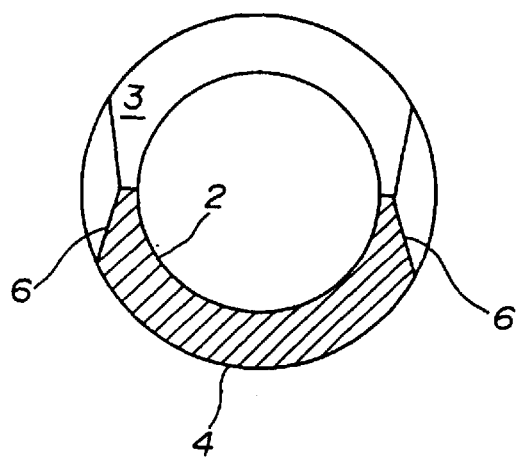
FIG. 5 is a view corresponding to FIG. 4, of another embodiment.

The right and left rear ground surfaces 6 do not necessarily have to be at a right angle with respect to the horizontal plane. As shown in FIG. 5, a case is considered where the right and left rear ground surfaces 6 tilt at an angle within a range of 5π/12 to π/2 radians (75 to 90 degrees) with respect to the horizontal plane. In this case, the upper and lower protruding corners of trapezoidal profiles are formed by the right and left rear ground surfaces 6 crossing the open bevel end surface 3 and crossing the external circumferential surface 4 of the bevel needle 1, respectively. Then, both of the upper and lower protruding corners have respective angles equal to, or greater than, a right angle, whereby neither of the right and left sides of the front-end portion 2 behind the front ends 8 of the right and left rear ground surfaces 6 form cutting edges.

When a dura mater or a blood vessel is punctured using the bevel needle 1, first, the right and left acute cutting edges 9 at the front end of the bevel needle 1 cut the dura mater or blood vessel wall in the shape of a circular arc that is close to a straight line, having a central angle of π/3 radians (60 degrees) or less. Next, the front-end portion behind the cutting edges 9 presses open the wound caused by the cutting edges 9 to penetrate therethrough, whereby an entire open bevel end surface enters into the subdural space or the inside of the blood vessel.

Thus, the front-end portion 2 of the bevel needle 1 forms a wound of the shape of a circular arc close to a straight line in the bio-tissue, when punctured. Because the wound of the shape of a circular arc having a narrow central angle would not curl up, the inside spinal fluid and the injected medicinal solution are not likely to leak out of the wound, and a quick recovery from the wound is also enabled. Consequently, a long-time pain is not likely to be inflicted on the patient after puncturing.

Figure 6:
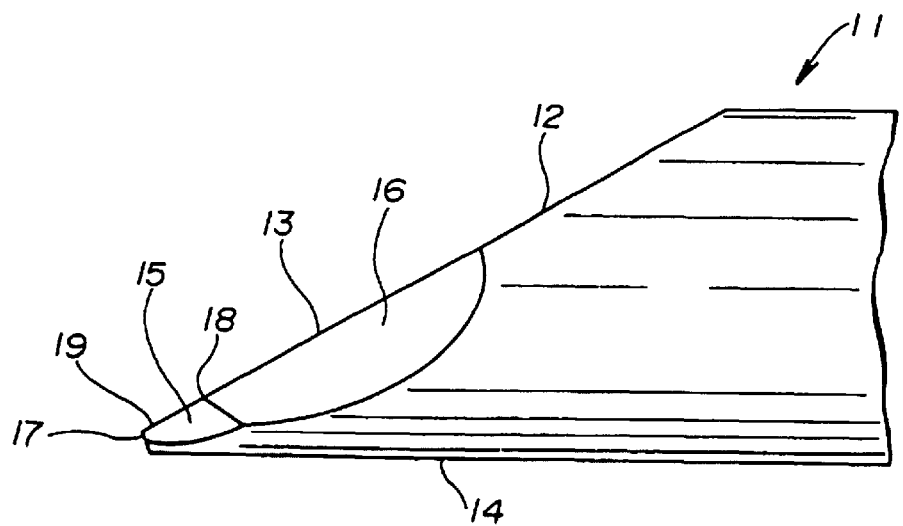
FIG. 6 is a side view of a second embodiment.
Figure 7:
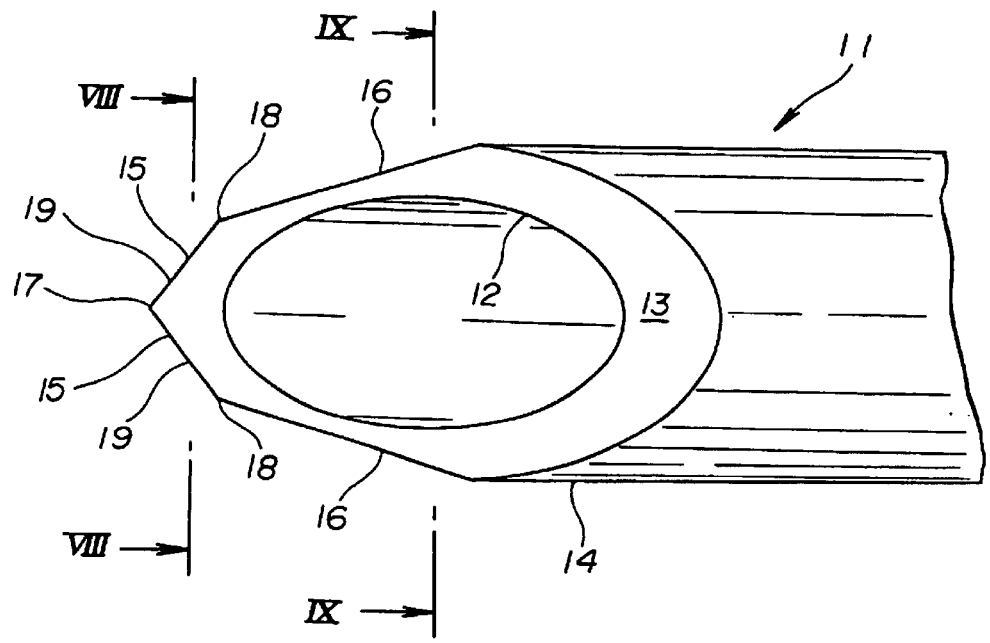
FIG. 7 is a plan view of the second embodiment.

As shown in FIGS. 6 and 7, the front-end portion 12 of a hollow bevel needle 11 of a second embodiment of the present invention includes the open bevel end surface 13, the external circumferential surface 14 of the bevel needle 1, right and left front ground surfaces 15, and right and left rear ground surfaces 16. When the needle axis is held horizontal with an open bevel end surface 13 facing upward, the open bevel end surface 13 crosses the vertical plane containing the needle axis at a right angle, and tilts backward at an angle of about $\pi/6$ radians (about 30 degrees) with respect to the horizontal plane. The right and left rear ground surfaces 16 cross the horizontal plane at a right angle, and tilt at an angle of about $\pi/12$ radians (about 15 degrees) with respect to the vertical plane. The right and left front ground surfaces 15 are right and left slopes symmetrical with respect to the vertical plane containing the needle axis, that tilt inward, with the lower and front ends thereof tilted toward the vertical plane. The right and left front ground surfaces 15 cross each other at the front end thereof and form a forward-tilting front edge line 17, with the upper end thereof positioned forward relative to the lower end thereof. The right and left front ground surfaces 15 also form cutting edges 19 that extend diagonally rearwardly on the right and left, by crossing the open bevel end surface 13.

The right and left rear ground surfaces 16 tilt symmetrically at an angle smaller than the angle of the right and left front ground surfaces 15 with respect to the vertical plane, and cross the horizontal plane at a right angle. The lateral width between the front ends 18 of the right and left rear ground surfaces 16 is equal to, or less than, the radius of the bevel needle.

Figure 8:
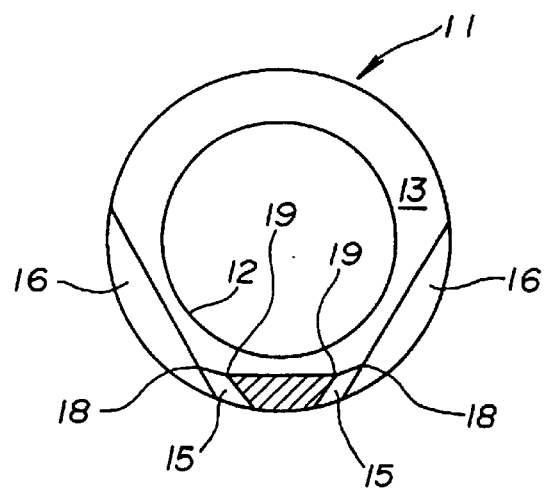
FIG. 8 is a cross-sectional view along arrow lines VIII—VIII of FIG. 7.
Figure 9:
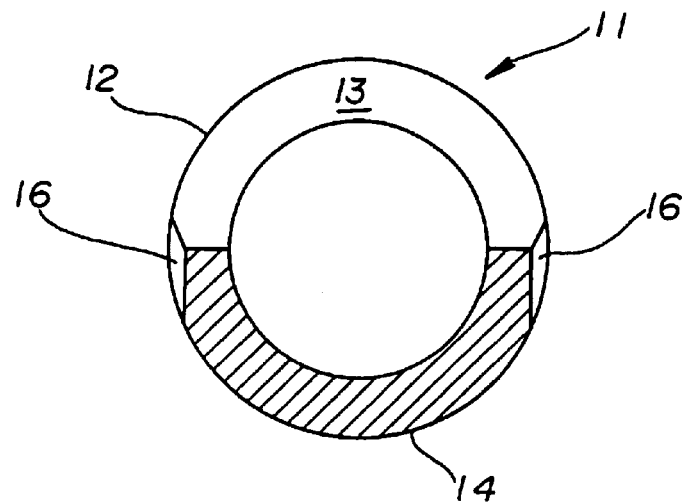
FIG. 9 is a cross-sectional view along arrow lines IX—IX of FIG. 7.

As shown in FIG. 8, at longitudinal positions ahead of the front end 18 of the right and left rear ground surfaces 16 of the front-end portion 12, the right and left front ground surfaces 15 and the external circumferential surface 14 of the bevel needle 11 protrude right-and leftwards, forming respective triangle-like profiles, in cross sections crossing the needle axis at a right angle. Because of having an acute apex angle, the triangle-like profiles form respective acute cutting edges 19. As shown in FIG. 9, however, at longitudinal positions behind the front end 18 of the right and left rear ground surfaces 16 on the front-end portion 12, both sides of the front-end portion 12 include the open bevel end surface 13, the right and left rear ground surfaces 16 and the external circumferential surface 14 of the bevel needle 11, and protrude right-and leftwards, forming respective trapezoidal profiles, in cross sections crossing the needle axis at a right angle. Because of the two corners thereof each having a right angle in the upper corner and an obtuse angle in the lower corner thereof, these trapezoidal profiles do not form cutting edges.

Figure 10:
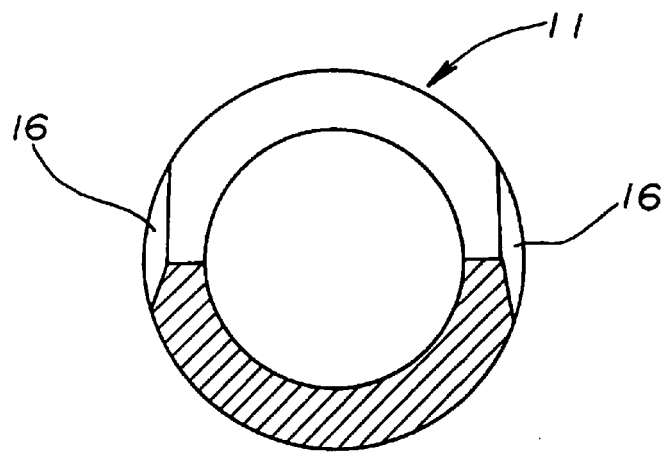
FIG. 10 is a view corresponding to FIG. 9, of another embodiment.

The right and left rear ground surfaces 16 do not necessarily have to be at a right angle with respect to the horizontal plane. As shown in FIG. 10, a case is considered where the right and left rear ground surfaces 16 tilt inward at an angle within a range of $5\pi/12$ to $\pi/2$ radians (75 to 90 degrees) with respect to the horizontal plane. In this case, both of the upper and lower protruding corners also have an angle equal to, or greater than, a right angle.

The front-end portion 12 of the bevel needle 11 forms a wound of the shape of a circular arc close to a straight line in the bio-tissue, when punctured. Because the wound of the shape of a circular arc having a narrow central angle would not curl up, the inside spinal fluid and the injected medicinal solution are not likely to leak out of the wound, and a quick recovery from the wound is also enabled. Consequently, a long-time pain is not likely to be inflicted on the patient after puncturing.

What is claimed is:

1. A medical bevel needle (1, 11) having an open bevel end surface (3, 13) on the front-end portion (2, 12) thereof, CHARACTERIZED IN THAT, when the needle axis is held horizontal with said open bevel end surface (3, 13) facing upward, said bevel needle (1, 11) comprises:

(A) right and left front ground surfaces (5, 15), disposed on said front-end portion (2, 12), respectively positioned right and left with respect to a vertical plane containing said needle axis, said right and left front ground surfaces (5, 15) crossing each other at the front end of said front-end portion (2, 12) of said bevel needle (1, 11), extending diagonally rearwardly and symmetrically with respect to said vertical plane; and (B) right and left rear ground surfaces (6, 16), disposed on said front-end portion (2, 12), said right and left rear ground surfaces (6, 16) respectively succeeding said right and left front ground surfaces (5, 15) at a longitudinal position where the lateral width between said right and left front ground surfaces (5, 15) reaches a specified length, said right and left rear ground surfaces (6, 16) extending diagonally rearwardly and symmetrically with respect to said vertical plane at an angle smaller than the angle of said right and left front ground surfaces (5, 15) with respect to said vertical plane, said right and left rear ground surfaces (6, 16) respectively having a tilt angle of $5\pi/12$ to $\pi/2$ radians (75 to 90 degrees) with respect to the horizontal plane;

said right and left rear ground surfaces (6, 16) limiting the maximum lateral width between cutting edges (9, 19), said cutting edges (9, 19) being formed either by said right and left front ground surfaces crossing the external circumferential surface (4, 14) of said bevel needle (1) or by said right and left front ground surfaces crossing said open bevel end surface;

said right and left rear ground surfaces (6, 16) respectively succeed said right and left front ground surfaces (5, 15) at a longitudinal position where the lateral width between said right and left front ground surfaces (5, 15) reaches a length equal to, or slightly smaller than, the radius of said bevel needle (1, 11).

2. A medical bevel needle (1) according to claim 1, CHARACTERIZED IN THAT:

said right and left front ground surfaces (5) form a backward-tilting front edge line (7) by crossing each other, and respectively form said cutting edges (9) by crossing said external circumferential surface (4) of said bevel needle (1).

3. A medical bevel needle (11) according to claim 1, CHARACTERIZED IN THAT:

said right and left front ground surfaces (15) form a forward-tilting front edge line (17) by crossing each other, and respectively form said cutting edges (19) by crossing said open bevel end surface (13) of said bevel needle (11).

4. A medical bevel needle (1, 11) according to claim 1, CHARACTERIZED IN THAT:

said open bevel end surface (3, 13) crosses said vertical plane at a right angle, and tilts backward at an angle of $\pi/9$ to $\pi/4$ radians (20 to 45 degrees with respect to the horizontal plane.

5. A medical bevel needle (1, 11) according to claim 4, CHARACTERIZED IN THAT:

said right and left rear ground surfaces (6, 16) cross the horizontal plane at a right angle, and tilts at an angle of about π/12 radians (about 15 degrees) with respect to the vertical plane.

6. A medical bevel needle (1, 11) according to claim 2, CHARACTERIZED IN THAT:

said open bevel end surface (3, 13) crosses said vertical plane at a right angle, and tilts backward at an angle of π/9 to π/4 radians (20 to 45 degrees with respect to the horizontal plane.

7. A medical bevel needle (1, 11) according to claim 3, CHARACTERIZED IN THAT:

said open bevel end surface (3, 13) crosses said vertical plane at a right angle, and tilts backward at an angle of π/9 to π/4 radians (20 to 45 degrees with respect to the horizontal plane.

* * * * *